(12) United States Patent
Fan et al.

(10) Patent No.: US 8,979,865 B2
(45) Date of Patent: Mar. 17, 2015

(54) COMPOSITE INTERFERENCE SCREWS AND DRIVERS

(75) Inventors: Wei Li Fan, Malden, MA (US); Paul Steven Vincuilla, Brockton, MA (US); Richard Mark Lunn, Kingston, MA (US); Mark Edwin Housman, North Attleborough, MA (US); Rebecca Blough, West Warwick, RI (US)

(73) Assignee: Smith & Nephew, Inc., Memphis, TN (US)

( * ) Notice: Subject to any disclaimer, the term of this patent is extended or adjusted under 35 U.S.C. 154(b) by 247 days.

(21) Appl. No.: 13/044,777

(22) Filed: Mar. 10, 2011

(65) Prior Publication Data

US 2012/0059384 A1 Mar. 8, 2012

Related U.S. Application Data

(60) Provisional application No. 61/312,291, filed on Mar. 10, 2010, provisional application No. 61/359,080, filed on Jun. 28, 2010, provisional application No. 61/334,808, filed on May 14, 2010.

(51) Int. Cl.
*A61B 17/58* (2006.01)
*A61B 17/86* (2006.01)
(Continued)

(52) U.S. Cl.
CPC ............ *A61F 2/0811* (2013.01); *A61F 2/0805* (2013.01); *A61F 2002/0841* (2013.01); *A61F 2002/0858* (2013.01); *A61F 2002/0888* (2013.01); *A61F 2250/0097* (2013.01); *A61B 17/0401* (2013.01); *A61B 2017/0409* (2013.01); *A61B 2017/044* (2013.01); *A61B 2017/0458* (2013.01)
USPC ............ 606/104; 606/301; 606/304; 606/321

(58) Field of Classification Search
USPC ................... 606/104, 300–321; 81/459–461
See application file for complete search history.

(56) References Cited

U.S. PATENT DOCUMENTS

| 3,499,222 A | 3/1970 | Linkow et al. | |
| 3,869,942 A * | 3/1975 | DeCaro | 81/54 |
| 4,177,797 A | 12/1979 | Baylis et al. | |

(Continued)

FOREIGN PATENT DOCUMENTS

| CN | 1829479 A | 9/2006 |
| CN | 101031248 A | 9/2007 |

(Continued)

OTHER PUBLICATIONS

International Search Report and Written Opinion for PCT/US2009/065304 Dated Mar. 8, 2010.

(Continued)

*Primary Examiner* — Nicholas Woodall
(74) *Attorney, Agent, or Firm* — Burns & Levinson, LLP; Joseph M. Maraia

(57) ABSTRACT

The present disclosure relates to a delivery device. The delivery device including a handle assembly, the assembly including a handle and a connector coupled to the handle, the connector including a channel and an opening to the channel; and a shaft coupled to the handle, the shaft including a proximal end and a distal end, the distal end including threads, grooves intersecting the threads, and a depth stop. Other delivery devices, screws, and delivery device/screw combinations are also disclosed.

17 Claims, 17 Drawing Sheets

(51) Int. Cl.
*A61F 2/08* (2006.01)
*A61B 17/04* (2006.01)

(56) References Cited

U.S. PATENT DOCUMENTS

| | | | |
|---|---|---|---|
| 4,653,489 A | 3/1987 | Tronzo | |
| 4,741,651 A | 5/1988 | Despres | |
| 4,834,757 A | 5/1989 | Brantigan | |
| 4,854,311 A | 8/1989 | Steffee | |
| 4,913,143 A | 4/1990 | Oloff et al. | |
| 4,961,740 A | 10/1990 | Ray et al. | |
| 5,026,373 A | 6/1991 | Ray et al. | |
| 5,055,104 A | 10/1991 | Ray | |
| 5,116,337 A | 5/1992 | Johnson | |
| 5,129,904 A | 7/1992 | Illi | |
| 5,129,906 A | 7/1992 | Ross et al. | |
| 5,197,967 A | 3/1993 | Wilson | |
| 5,236,431 A | 8/1993 | Gogolewski et al. | |
| 5,242,447 A | 9/1993 | Borzone | |
| 5,354,299 A | 10/1994 | Coleman | |
| 5,364,400 A | 11/1994 | Rego, Jr. et al. | |
| 5,383,878 A | 1/1995 | Roger et al. | |
| 5,407,427 A | 4/1995 | Zhu et al. | |
| 5,411,523 A | 5/1995 | Goble | |
| 5,447,533 A | 9/1995 | Vachon et al. | |
| 5,464,427 A | 11/1995 | Curtis et al. | |
| 5,470,334 A | 11/1995 | Ross et al. | |
| 5,531,780 A | 7/1996 | Vachon | |
| 5,571,139 A | 11/1996 | Jenkins, Jr. | |
| 5,593,409 A | 1/1997 | Michelson | |
| 5,609,635 A | 3/1997 | Michelson | |
| 5,626,613 A | 5/1997 | Schmieding | |
| 5,645,547 A * | 7/1997 | Coleman | 606/304 |
| 5,658,285 A | 8/1997 | Mamay et al. | |
| 5,676,545 A | 10/1997 | Jones | |
| 5,681,352 A | 10/1997 | Clancy, III et al. | |
| 5,688,285 A | 11/1997 | Yamada | |
| 5,695,497 A | 12/1997 | Stahelin | |
| 5,709,683 A | 1/1998 | Bagby | |
| 5,802,794 A | 9/1998 | Robson | |
| 5,833,715 A | 11/1998 | Vachon et al. | |
| 5,888,227 A | 3/1999 | Cottle | |
| 5,891,146 A | 4/1999 | Simon et al. | |
| 5,921,982 A | 7/1999 | Lesh et al. | |
| 5,951,560 A | 9/1999 | Simon et al. | |
| 5,961,524 A | 10/1999 | Crombie | |
| 5,964,783 A | 10/1999 | Grafton et al. | |
| 5,968,047 A | 10/1999 | Reed | |
| 5,968,098 A | 10/1999 | Winslow | |
| 5,984,967 A | 11/1999 | Zdeblick et al. | |
| 6,008,433 A | 12/1999 | Stone | |
| 6,039,762 A | 3/2000 | McKay | |
| 6,086,593 A | 7/2000 | Bonutti | |
| 6,096,060 A | 8/2000 | Fitts et al. | |
| 6,097,986 A | 8/2000 | Janke et al. | |
| 6,196,780 B1 | 3/2001 | Wakai et al. | |
| 6,235,057 B1 | 5/2001 | Roger et al. | |
| 6,283,973 B1 * | 9/2001 | Hubbard et al. | 606/104 |
| 6,360,129 B1 | 3/2002 | Ley et al. | |
| 6,443,989 B1 | 9/2002 | Jackson | |
| 6,447,545 B1 | 9/2002 | Bagby | |
| 6,488,683 B2 | 12/2002 | Lieberman | |
| 6,514,257 B2 | 2/2003 | Dovesi et al. | |
| 6,517,542 B1 | 2/2003 | Papay et al. | |
| 6,527,774 B2 | 3/2003 | Lieberman | |
| 6,544,265 B2 | 4/2003 | Lieberman | |
| 6,551,319 B2 | 4/2003 | Lieberman | |
| 6,551,320 B2 | 4/2003 | Lieberman | |
| 6,551,322 B1 | 4/2003 | Lieberman | |
| 6,554,830 B1 | 4/2003 | Chappius | |
| 6,589,245 B1 | 7/2003 | Weiler et al. | |
| 6,626,917 B1 | 9/2003 | Craig | |
| 6,823,871 B2 | 11/2004 | Schmieding | |
| 6,855,168 B2 | 2/2005 | Crozet | |
| 6,863,671 B1 | 3/2005 | Strobel et al. | |
| 6,953,462 B2 | 10/2005 | Lieberman | |
| 7,033,372 B1 | 4/2006 | Cahalan | |
| 7,070,586 B2 | 7/2006 | Hart et al. | |
| 7,083,647 B1 | 8/2006 | Sklar et al. | |
| 7,189,251 B2 | 3/2007 | Kay | |
| 7,195,634 B2 | 3/2007 | Schmieding et al. | |
| 7,217,279 B2 | 5/2007 | Reese | |
| 7,322,986 B2 | 1/2008 | Wolf | |
| 7,594,929 B2 | 9/2009 | Collette | |
| 7,608,098 B1 | 10/2009 | Stone et al. | |
| 7,867,252 B2 | 1/2011 | Criscuolo et al. | |
| 7,914,539 B2 | 3/2011 | Stone et al. | |
| 8,016,865 B2 | 9/2011 | Donnelly et al. | |
| 8,034,090 B2 | 10/2011 | Stone et al. | |
| 8,636,799 B2 | 1/2014 | Sklar et al. | |
| 8,672,967 B2 | 3/2014 | DiMatteo | |
| 2002/0022862 A1 | 2/2002 | Grafton et al. | |
| 2002/0055737 A1 | 5/2002 | Lieberman | |
| 2002/0055738 A1 | 5/2002 | Lieberman | |
| 2002/0055742 A1 | 5/2002 | Lieberman | |
| 2002/0087189 A1 | 7/2002 | Bonutti | |
| 2002/0087190 A1 | 7/2002 | Benavitz et al. | |
| 2002/0099382 A1 | 7/2002 | Salazar et al. | |
| 2002/0143335 A1 | 10/2002 | von Hoffmann et al. | |
| 2002/0165546 A1 | 11/2002 | Goble et al. | |
| 2003/0055431 A1 | 3/2003 | Brannon | |
| 2003/0065374 A1 | 4/2003 | Honeck | |
| 2003/0069640 A1 | 4/2003 | Ferreora et al. | |
| 2003/0125749 A1 | 7/2003 | Yuan et al. | |
| 2003/0181913 A1 | 9/2003 | Lieberman | |
| 2004/0015170 A1 | 1/2004 | Tallarida | |
| 2004/0030343 A1 | 2/2004 | Kurc | |
| 2004/0039404 A1 | 2/2004 | Dreyfuss | |
| 2004/0073216 A1 | 4/2004 | Lieberman | |
| 2004/0097945 A1 | 5/2004 | Wolf | |
| 2004/0122424 A1 | 6/2004 | Ferree | |
| 2004/0143158 A1 | 7/2004 | Hart et al. | |
| 2004/0143237 A1 | 7/2004 | Hart et al. | |
| 2004/0153074 A1 | 8/2004 | Bojarski et al. | |
| 2004/0267265 A1 | 12/2004 | Kyle | |
| 2005/0107828 A1 | 5/2005 | Reese | |
| 2005/0159727 A1 | 7/2005 | Lesh | |
| 2005/0222681 A1 | 10/2005 | Richley et al. | |
| 2005/0234458 A1 | 10/2005 | Huebner | |
| 2005/0250984 A1 | 11/2005 | Lam et al. | |
| 2005/0250985 A1 | 11/2005 | Saadat et al. | |
| 2005/0250987 A1 | 11/2005 | Ewers et al. | |
| 2005/0250988 A1 | 11/2005 | Ewers et al. | |
| 2005/0283239 A1 | 12/2005 | Crozet | |
| 2006/0009769 A1 | 1/2006 | Lieberman | |
| 2006/0030948 A1 | 2/2006 | Manrique et al. | |
| 2006/0079895 A1 | 4/2006 | McLeer | |
| 2006/0100627 A1 | 5/2006 | Stone et al. | |
| 2006/0106390 A1 | 5/2006 | Jensen et al. | |
| 2006/0142769 A1 | 6/2006 | Collette | |
| 2006/0149266 A1 | 7/2006 | Cordasco | |
| 2006/0217681 A1 | 9/2006 | Hart et al. | |
| 2006/0241636 A1 | 10/2006 | Novak et al. | |
| 2006/0247642 A1 | 11/2006 | Stone et al. | |
| 2006/0253080 A1 | 11/2006 | Tulleken et al. | |
| 2006/0276841 A1 | 12/2006 | Barbieri et al. | |
| 2007/0032797 A1 | 2/2007 | Ortiz et al. | |
| 2007/0093895 A1 | 4/2007 | Donnelly et al. | |
| 2007/0122764 A1 | 5/2007 | Balfour et al. | |
| 2007/0142849 A1 | 6/2007 | Ewers et al. | |
| 2007/0185532 A1 | 8/2007 | Stone et al. | |
| 2007/0198019 A1 | 8/2007 | Schomer et al. | |
| 2008/0027446 A1 | 1/2008 | Stone et al. | |
| 2008/0065114 A1 | 3/2008 | Stone et al. | |
| 2008/0082128 A1 | 4/2008 | Stone | |
| 2008/0132932 A1 | 6/2008 | Hoeppner et al. | |
| 2008/0140092 A1 | 6/2008 | Stone et al. | |
| 2008/0140093 A1 | 6/2008 | Stone et al. | |
| 2008/0154314 A1 | 6/2008 | McDevitt | |
| 2008/0179839 A1 * | 7/2008 | Walters | 279/51 |
| 2009/0024174 A1 | 1/2009 | Stark | |
| 2009/0042951 A1 | 2/2009 | Danziger | |
| 2009/0076544 A1 | 3/2009 | DiMatteo et al. | |
| 2009/0248029 A1 * | 10/2009 | Paulos | 606/104 |

(56) References Cited

U.S. PATENT DOCUMENTS

| | | |
|---|---|---|
| 2009/0319043 A1 | 12/2009 | McDevitt |
| 2010/0106166 A1 | 4/2010 | Cropper et al. |
| 2011/0112576 A1 | 5/2011 | Nguyen et al. |
| 2011/0224727 A1 | 9/2011 | Housman et al. |
| 2011/0282450 A1 | 11/2011 | Donnelly et al. |
| 2011/0319933 A1 | 12/2011 | Tepic |
| 2013/0150859 A1 | 6/2013 | Kehres et al. |
| 2013/0158596 A1 | 6/2013 | Miller et al. |
| 2013/0158597 A1 | 6/2013 | Hernandez |
| 2013/0158599 A1 | 6/2013 | Hester |
| 2013/0158610 A1 | 6/2013 | Hernandez |
| 2014/0142697 A1 | 5/2014 | Sklar et al. |
| 2014/0148850 A1 | 5/2014 | DiMatteo |

FOREIGN PATENT DOCUMENTS

| | | |
|---|---|---|
| EP | 0502698 B1 | 9/1992 |
| EP | 0538895 A2 | 4/1993 |
| EP | 0682917 B1 | 11/1995 |
| EP | 1147751 B1 | 10/2001 |
| EP | 1917926 A1 | 7/2008 |
| EP | 2036501 A3 | 9/2010 |
| EP | 2601894 A1 | 6/2013 |
| FR | 2760355 A1 | 9/1998 |
| FR | 2846867 A1 | 5/2004 |
| WO | 9608205 A1 | 3/1996 |
| WO | 9619947 A1 | 7/1996 |
| WO | 9802117 A1 | 1/1998 |
| WO | 9826717 A1 | 6/1998 |
| WO | WO2006055516 A | 5/2006 |
| WO | 2007093192 A1 | 8/2007 |
| WO | 2008021474 A2 | 2/2008 |
| WO | 2008100944 A1 | 8/2008 |
| WO | 2009/042951 A1 | 4/2009 |
| WO | 2009042951 A1 | 4/2009 |
| WO | 2010017631 A1 | 2/2010 |
| WO | 2011112776 A1 | 9/2011 |

OTHER PUBLICATIONS

Smith & Nephew brochure titled "BioRCITM Bioabsorbable Screws: Anatomically Targeted Screws for ACL and PCL Reconstruction", 2000.

Biomet brochure titled "Bio-CoreTM Interference Screw", 2007.

International Search and Written Opinion for PCT/US2011/027837mailed May 19, 2011.

Hunt, Patrick, D.V.M. et al. "Development of a Perforated Biodegradable Interference Screw", Arthroscopy: The Journal of Arthroscopic and Related Surgery, vol. 21, No. 3, Mar. 2005; pp. 258-265.

International Search and Written Opinion for PCT/US2012/041298 mailed Jun. 5, 2013.

International Search and Written Opinion for PCT/US2012/028803 mailed Oct. 24, 2010.

Notice of Reasons for Rejections for Japanese Patent Application No. 2011-538642, mailed Oct. 1, 2013.

First Office Action for Chinese Patent Application No. 200980155954.7, issued Apr. 12, 2013.

Second Office Action for Chinese Patent Application No. 200980155954.7, issued Oct. 24, 2013.

International Search and Written Opinion for PCT/US2014/022539 mailed Jun. 27, 2014.

International Search and Written Opinion for PCT/US2014/020747 mailed Jun. 6, 2014.

Decision of Rejections for Japanese Patent Application No. 2011-538642, mailed Jun. 14, 2014.

International Search and Written Opinion for PCT/US2014/033535 mailed Jul. 18, 2014.

First Office Action for Chinese Patent Application No. 201180013194.3, issued Jul. 21, 2014.

Japanese Office Action dated Nov. 25, 2014 in related Japanese application No. 2012-557236.

* cited by examiner

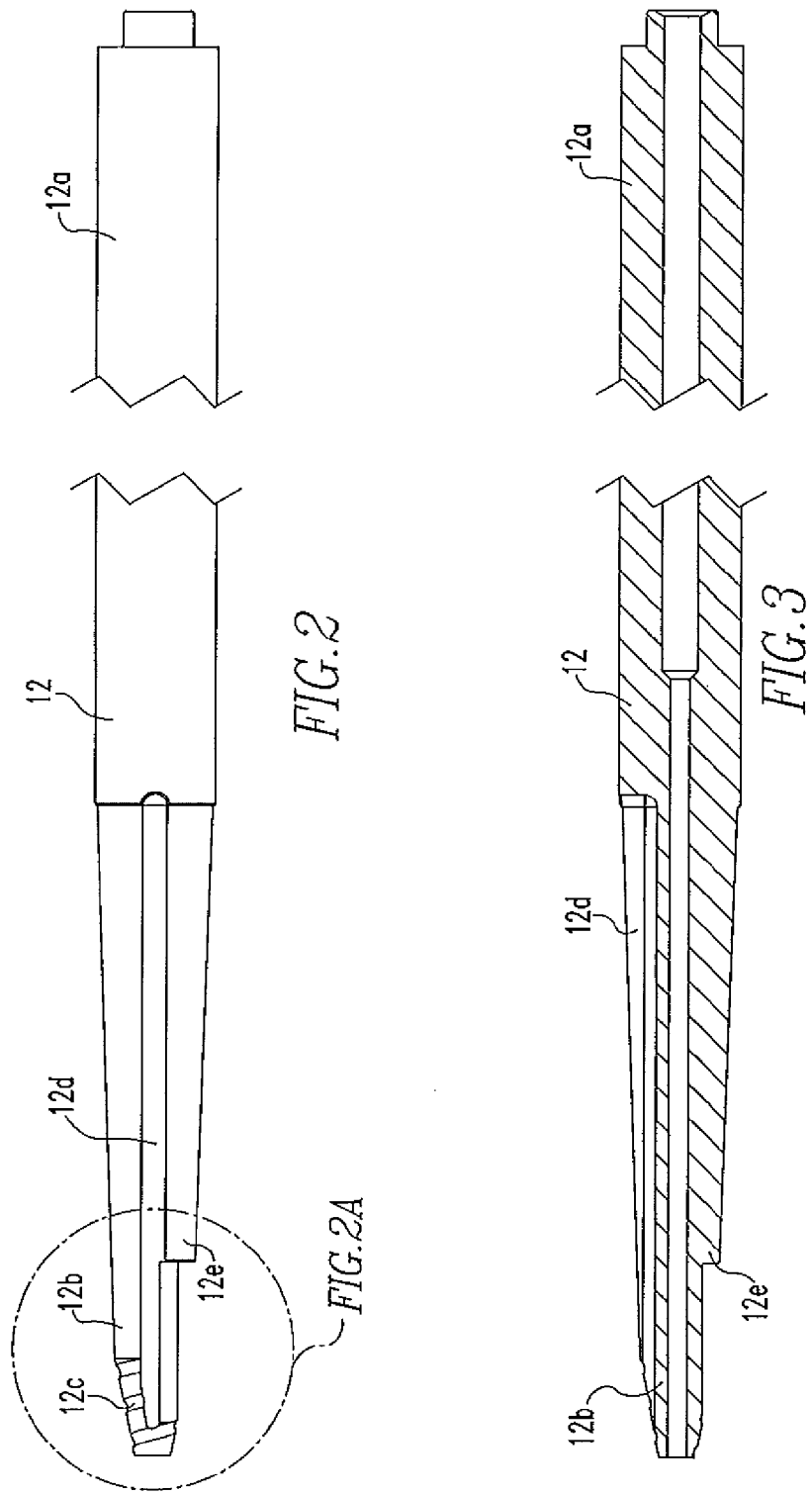

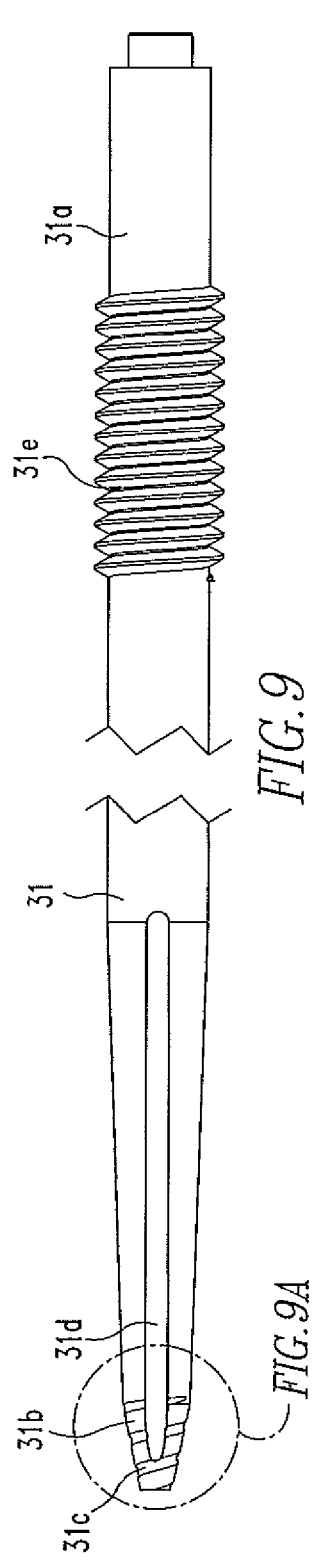
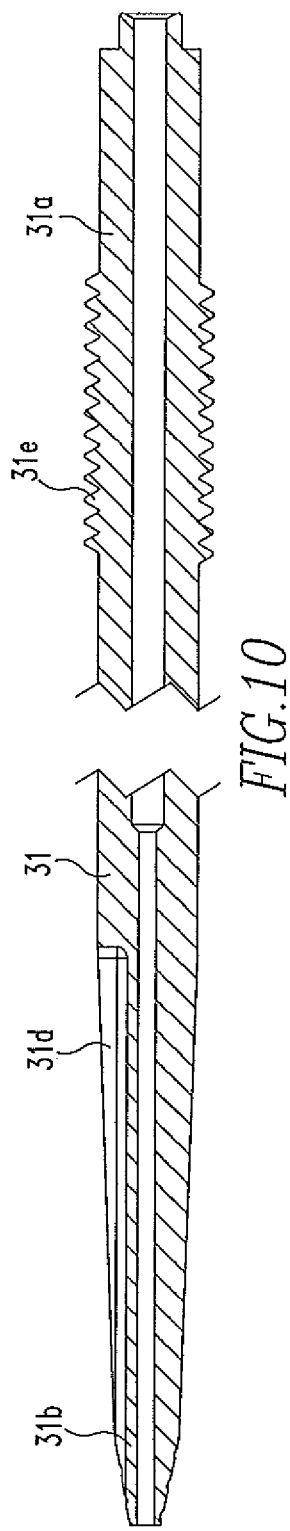

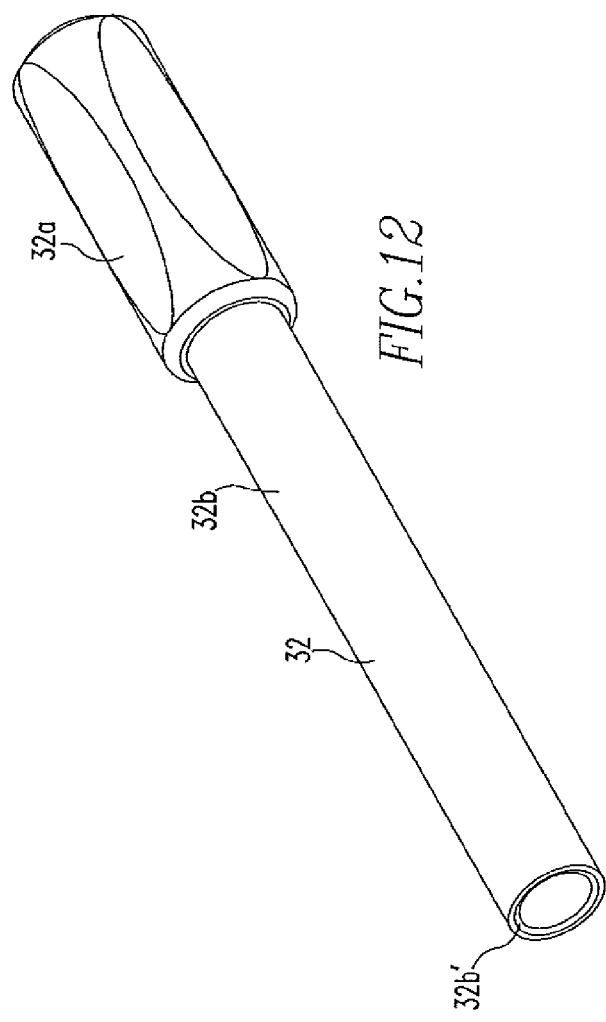
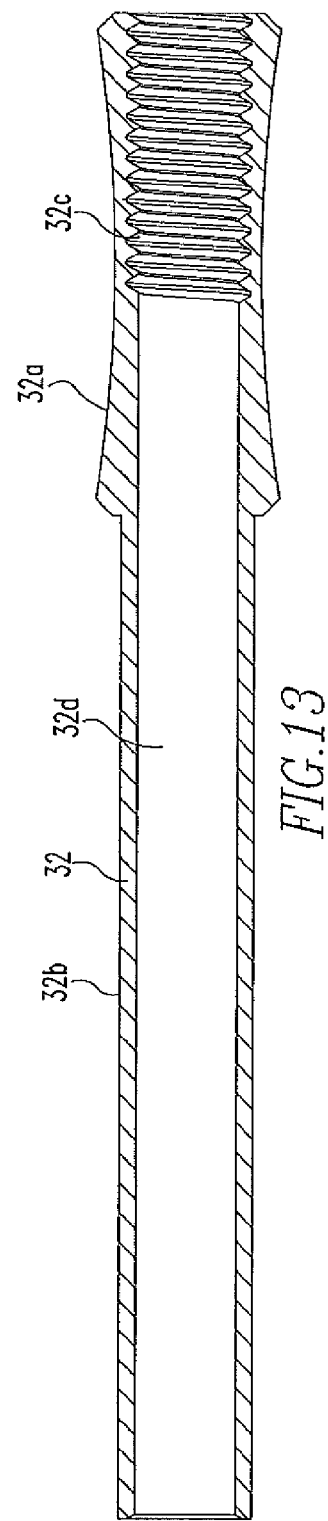

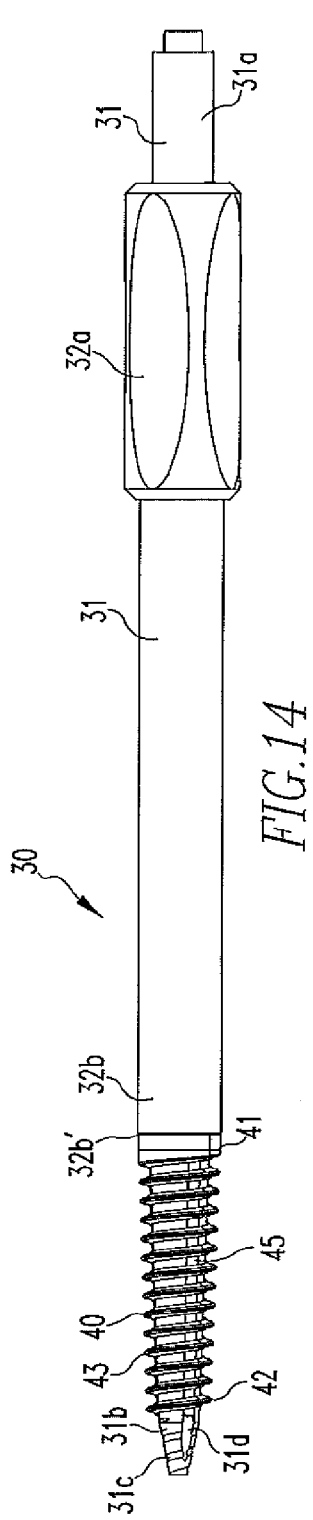
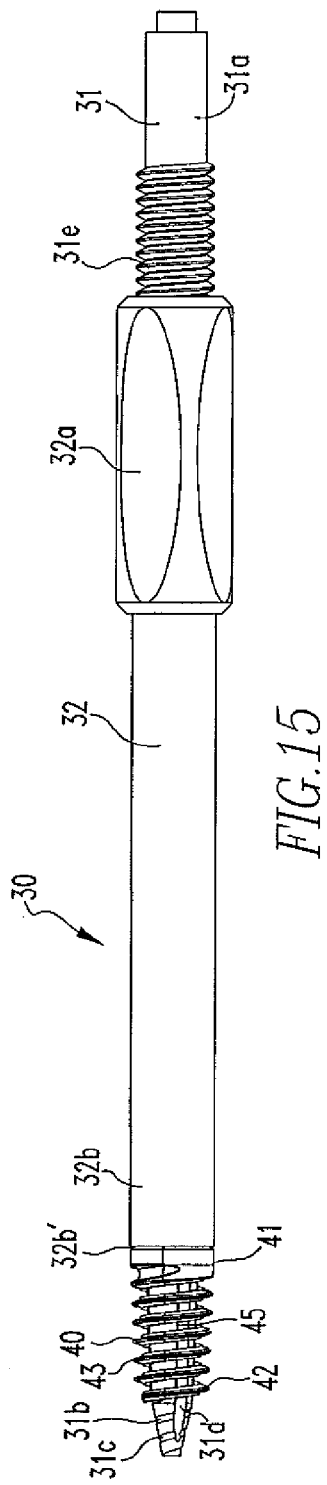
FIG.14
FIG.15

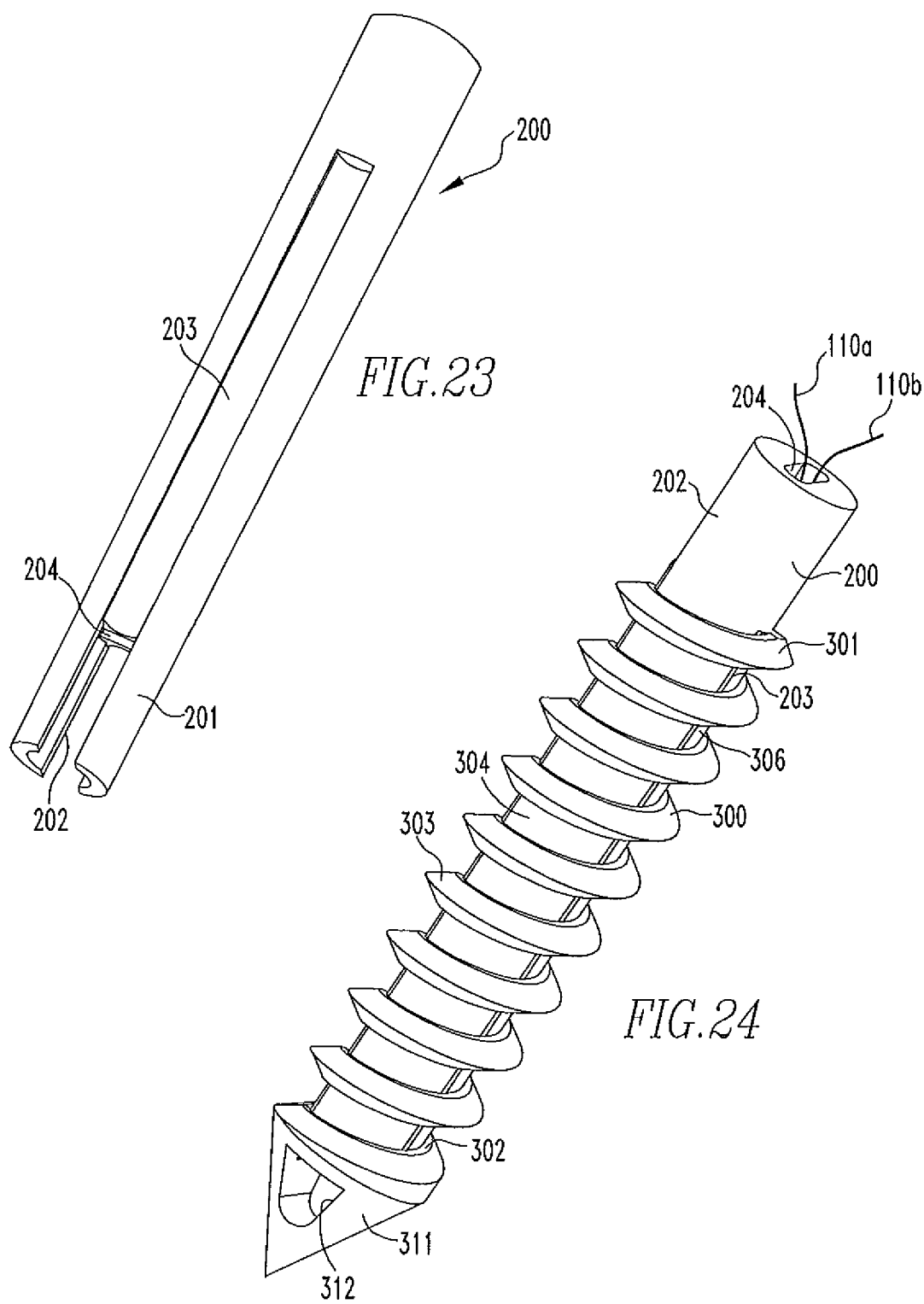

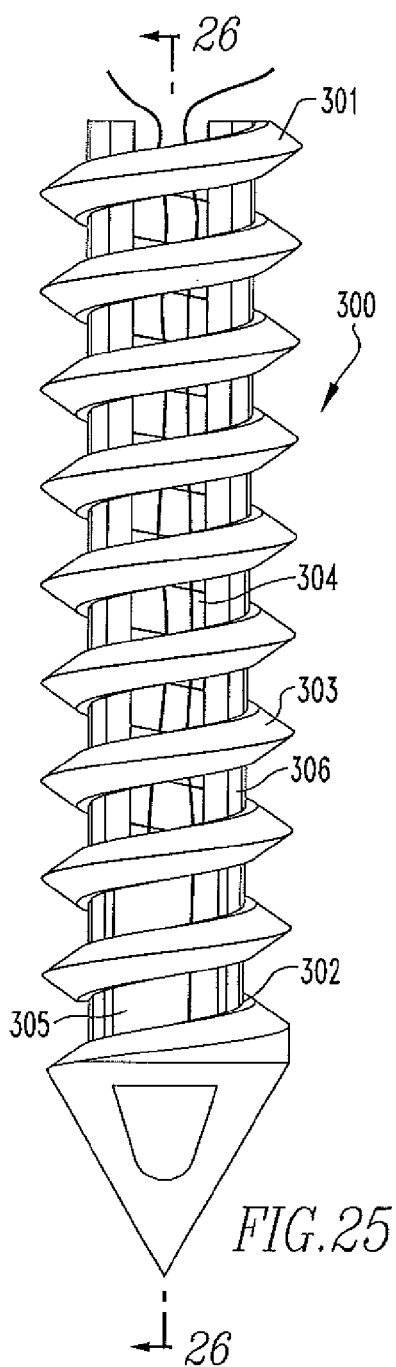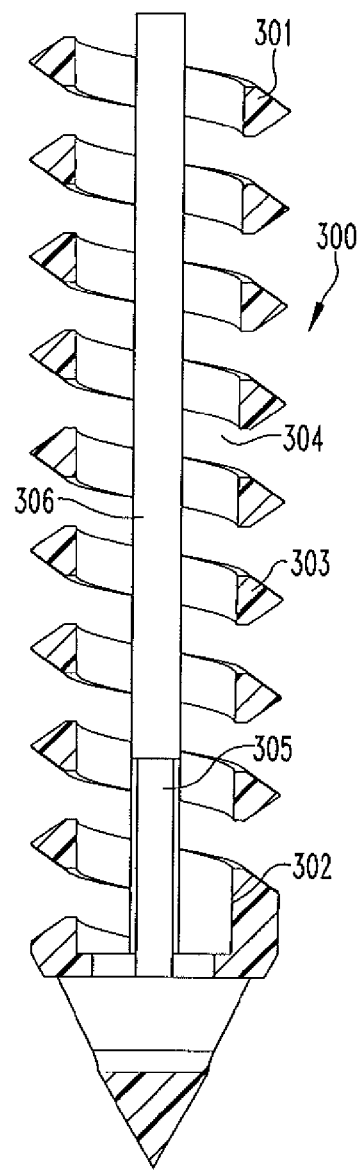
FIG.25
FIG.26

COMPOSITE INTERFERENCE SCREWS AND DRIVERS

CROSS-REFERENCE TO RELATED APPLICATIONS

This application claims priority to U.S. Patent Application Ser. No. 61/312,291, U.S. Patent Application Ser. No. 61/334,808, and U.S. Patent Application Ser. No. 61/359,080, the disclosures of which are incorporated herein by reference in their entireties.

BACKGROUND

1. Field of Technology

The present disclosure relates to medical apparatuses and procedures in general, and more particularly to medical apparatuses and procedures for reconstructing a ligament.

2. Related Art

In many cases, ligaments are torn or ruptured as the result of an accident. Accordingly, various procedures have been developed to repair or replace such damaged ligaments.

For example, in the human knee, the anterior and posterior cruciate ligaments (i.e., the "ACL" and "PCL") extend between the top end of the tibia and the bottom end of the femur. Often, the anterior cruciate ligament (i.e., the ACL) is ruptured or torn as the result of, for example, a sports-related injury. Consequently, various surgical procedures have been developed for reconstructing the ACL so as to restore substantially normal function to the knee.

In many instances, the ACL may be reconstructed by replacing the ruptured ACL with a graft ligament. More particularly, in such a procedure, bone tunnels are generally formed in both the top of the tibia and the bottom of the femur, with one end of the graft ligament being positioned in the femoral tunnel and the other end of the graft ligament being positioned in the tibial tunnel, and with the intermediate portion of the graft ligament spanning the distance between the bottom of the femur and the top of the tibia. The two ends of the graft ligament are anchored in their respective bone tunnels in various ways well known in the art so that the graft ligament extends between the bottom end of the femur and the top end of the tibia in substantially the same way, and with substantially the same function, as the original ACL. This graft ligament then cooperates with the surrounding anatomical structures so as to restore substantially normal function to the knee.

In some circumstances, the graft ligament may be a ligament or tendon which is harvested from elsewhere within the patient's body, e.g., a patella tendon with or without bone blocks attached, a semitendinosus tendon and/or a gracilis tendon.

As noted above, various approaches are well known in the art for anchoring the two ends of the graft ligament in the femoral and tibial bone tunnels.

In one well-known procedure, which may be applied to femoral fixation, tibial fixation, or both, the end of the graft ligament is placed in the bone tunnel, and then the graft ligament is fixed in place using a headless orthopedic screw, generally known in the art as an "interference" screw. More particularly, with this approach, the end of the graft ligament is placed in the bone tunnel and then the interference screw is advanced into the bone tunnel so that the interference screw extends parallel to the bone tunnel and simultaneously engages both the graft ligament and the side wall of the bone tunnel. In this arrangement, the interference screw essentially drives the graft ligament laterally, into engagement with the opposing side wall of the bone tunnel, whereby to secure the graft ligament to the host bone with a so-called "interference fit". Thereafter, over time (e.g., several months), the graft ligament and the host bone grow together at their points of contact so as to provide a strong, natural joinder between the ligament and the bone.

Interference screws have proven to be an effective means for securing a graft ligament in a bone tunnel. However, the interference screw itself generally takes up a substantial amount of space within the bone tunnel, which can limit the surface area contact established between the graft ligament and the side wall of the bone tunnel. This in turn limits the region of bone-to-ligament in-growth, and hence can affect the strength of the joinder. By way of example but not limitation, it has been estimated that the typical interference screw obstructs about 50% of the potential bone-to-ligament integration region.

For this reason, substantial efforts have been made to provide interference screws fabricated from absorbable materials, so that the interference screw can eventually disappear over time and bone-to-ligament in-growth can take place about the entire perimeter of the bone tunnel. To this end, various absorbable interference screws have been developed which are made from biocompatible, bioabsorbable polymers, e.g., polylactic acid (PLA), polyglycolic acid (PGA), etc. These polymers generally provide the substantial mechanical strength needed to advance the interference screw into position, and to thereafter hold the graft ligament in position while bone-to-ligament in-growth occurs, without remaining in position on a permanent basis.

In general, interference screws made from such biocompatible, bioabsorbable polymers have proven clinically successful. However, these absorbable interference screws still suffer from several disadvantages. First, clinical evidence suggests that the quality of the bone-to-ligament in-growth is somewhat different than natural bone-to-ligament in-growth, in the sense that the aforementioned bioabsorbable polymers tend to be replaced by a fibrous mass rather than a well-ordered tissue matrix. Second, clinical evidence suggests that absorption generally takes a substantial period of time, e.g., on the order of three years or so. Thus, during this absorption time, the bone-to-ligament in-growth is still significantly limited by the presence of the interference screw. Third, clinical evidence suggests that, for many patients, absorption is never complete, leaving a substantial foreign mass remaining within the body. This problem is exacerbated somewhat by the fact that absorbable interference screws generally tend to be fairly large in order to provide them with adequate strength, e.g., it is common for an interference screw to have a diameter (i.e., an outer diameter) of 8-12 mm and a length of 20-25 mm.

Thus, there is a need for a new and improved interference fixation system which (i) has the strength needed to hold the graft ligament in position while bone-to-ligament in-growth occurs, and (ii) promotes superior bone-to-ligament in-growth.

SUMMARY

In one aspect, the present disclosure relates to a delivery device. The delivery device including a handle assembly, the assembly including a handle and a connector coupled to the handle, the connector including a channel and an opening to the channel; and a shaft coupled to the handle, the shaft including a proximal end and a distal end, the distal end including threads, grooves intersecting the threads, and a depth stop.

In another aspect, the present disclosure relates to an interference screw. The interference screw includes a proximal end and a distal end, the screw including threads extending in an open helical form from the proximal end to the distal end, a depth stop extending a partial length of the screw, and a plurality of runners extending longitudinally along an interior of the screw.

In yet another aspect, the present disclosure relates to a delivery device and screw combination. The combination includes a delivery device including a handle assembly, the assembly including a handle and a connector coupled to the handle, the connector including a channel and an opening to the channel; and a shaft coupled to the handle, the shaft including a proximal end and a distal end, the distal end including threads, grooves intersecting the threads, and a depth stop; and an interference screw coupled to the delivery device comprising a proximal end and a distal end, the screw including threads extending in an open helical form from the proximal end to the distal end, a depth stop extending a partial length of the screw, and a plurality of runners extending longitudinally along an interior of the screw, the screw located on the distal end of the delivery device such that a proximal end of the depth stop of the screw engages the depth stop of the delivery device.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIG. 2 shows a side view of the shaft of the delivery device of FIG. 1.

FIG. 3 shows a cross-sectional view of the shaft of FIG. 2.

FIG. 9 shows a side view of the inner member of the shaft of FIG. 8.

FIG. 10 shows a cross-sectional view of the inner member of the shaft of FIG. 9.

FIG. 12 shows an isometric view of the outer member of the shaft of FIG. 8.

FIG. 13 shows a cross-sectional view of the outer member of FIG. 12.

FIGS. 14 and 15 show side views of the shaft of FIG. 8 with the outer member in different positions.

FIG. 23 shows an isometric view of the shaft of FIG. 21.

FIG. 24 shows an isometric view of the shaft of FIG. 21 and an alternative screw for use with the shaft.

FIG. 25 shows a side view of the screw of FIG. 24.

FIG. 26 shows a cross-sectional view of the screw of FIG. 24.

DETAILED DESCRIPTION OF THE EMBODIMENTS

The following description of the preferred embodiment(s) is merely exemplary in nature and is in no way intended to limit the disclosure, its application, or uses.

Figure 1:
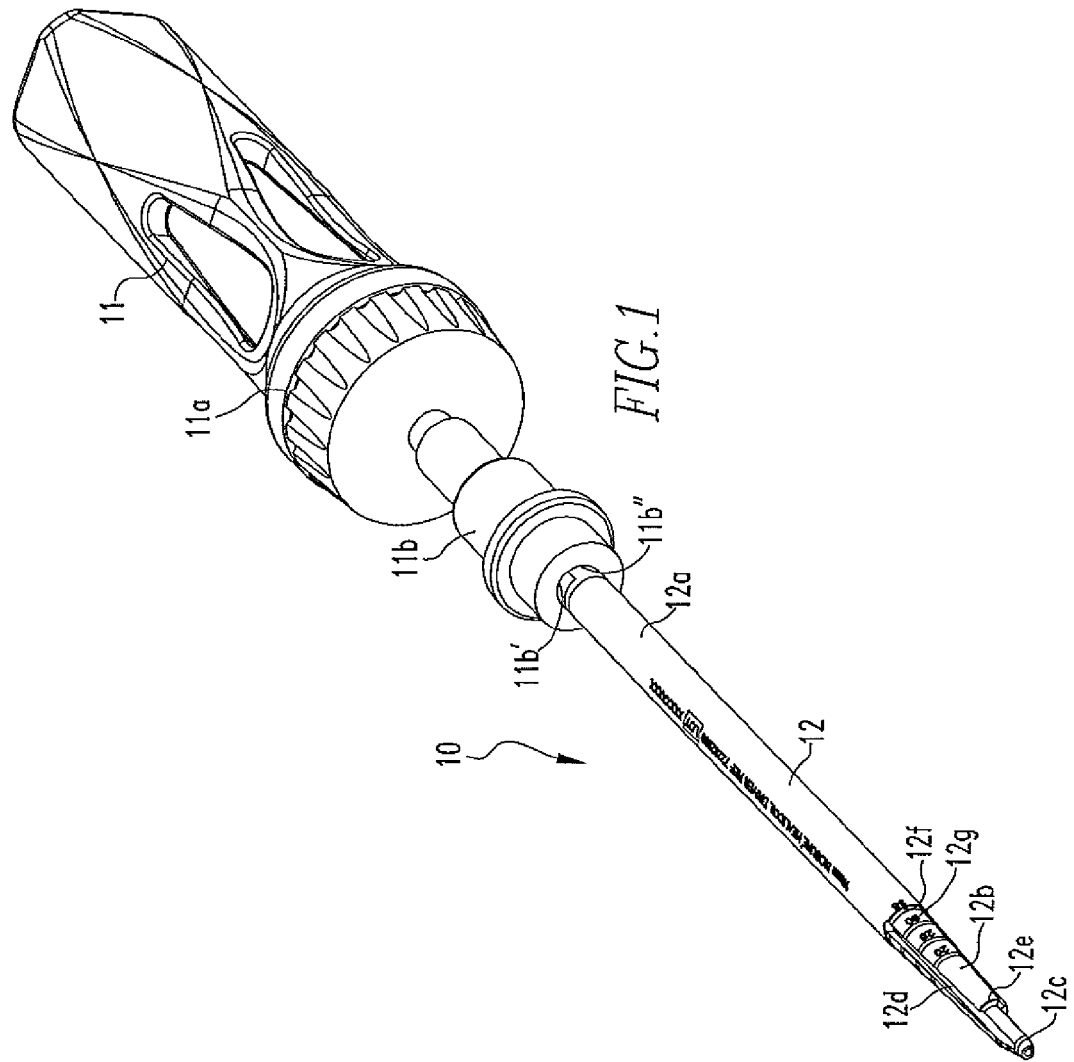
FIG. 1 shows a first embodiment of the delivery device of the present disclosure.
Figure 2A:
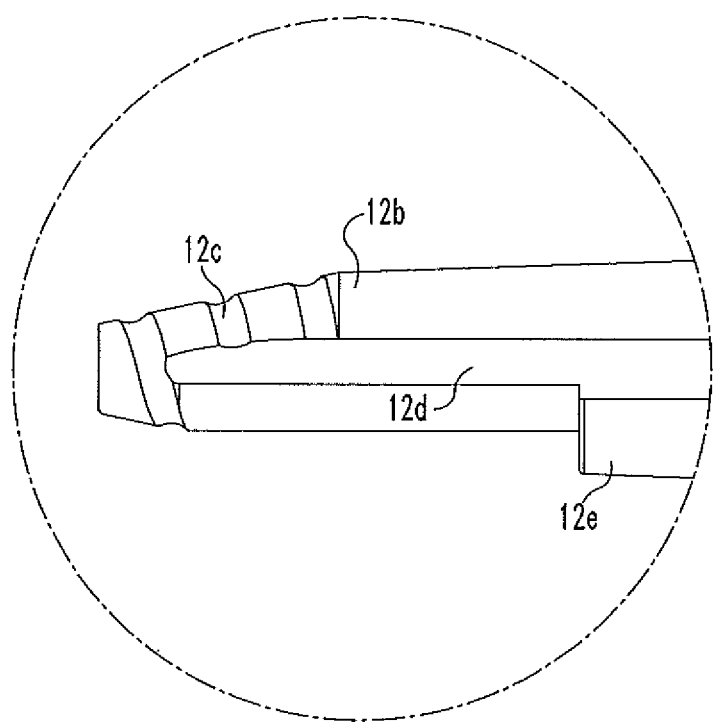
FIG. 2A shows an exploded view of the distal end of the shaft of FIG. 2.
Figure 4:
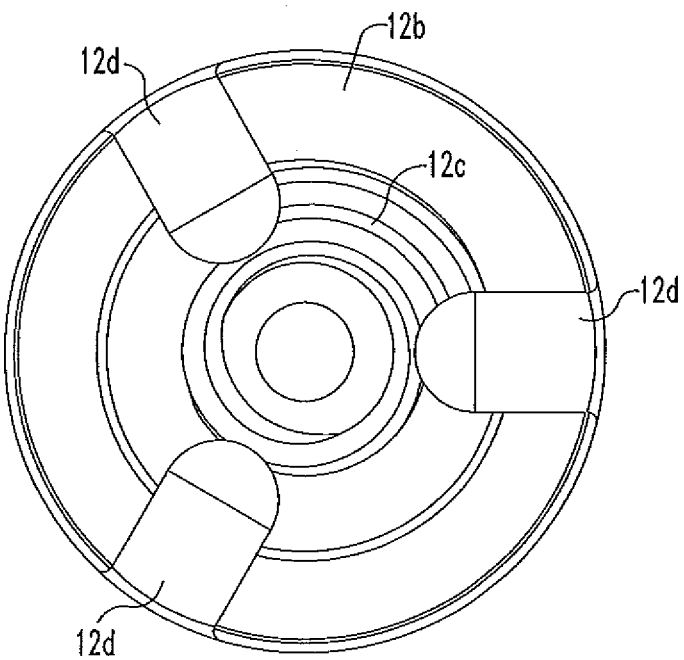
FIG. 4 shows a front view of the distal end of the shaft of FIG. 2.

FIG. 1 shows a first embodiment of the delivery device 10 of the present disclosure. The device 10 includes a handle assembly 11 and a shaft 12 coupled to the handle assembly 11. The handle assembly 11 includes a handle 11a and a connector 11b coupled to the handle 11a. The connector 11b has a channel 11b' and an opening 11b" to the channel 11b'. The opening 11b" is in the shape of a "D". A proximal end 12a of the shaft 12 is disposed within the channel 11b'.

FIGS. 2, 2A, and 3-4 show the shaft 12. The shaft 12 includes a proximal end 12a and a distal end 12b. The proximal end 12a is in the shape of a "D" to match the shape of the opening 11b". The distal end 12b includes threads 12c, grooves 12d, and a depth stop 12e. The grooves 12d extend a partial length of the shaft 12 and intersect the threads 12c. The depth stop 12e is for use with a depth stop on a screw that the device 10 is used to implant into a bone tunnel during ligament reconstruction surgery.

Figure 5:
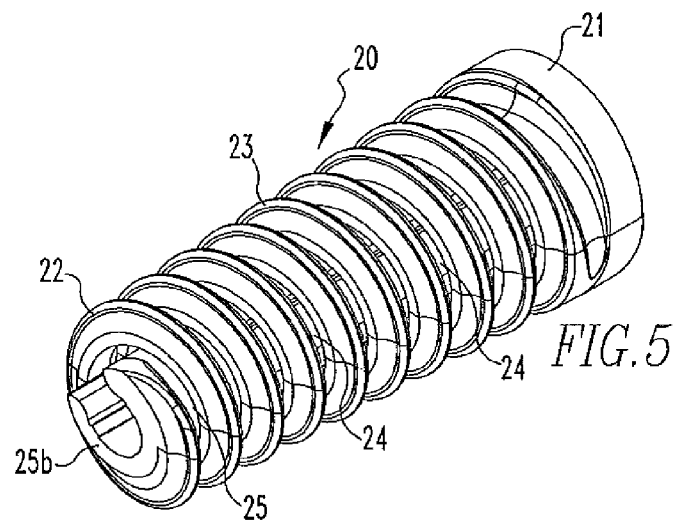
FIG. 5 shows an isometric view of the screw for use with the shaft of FIG. 2.
Figure 6:
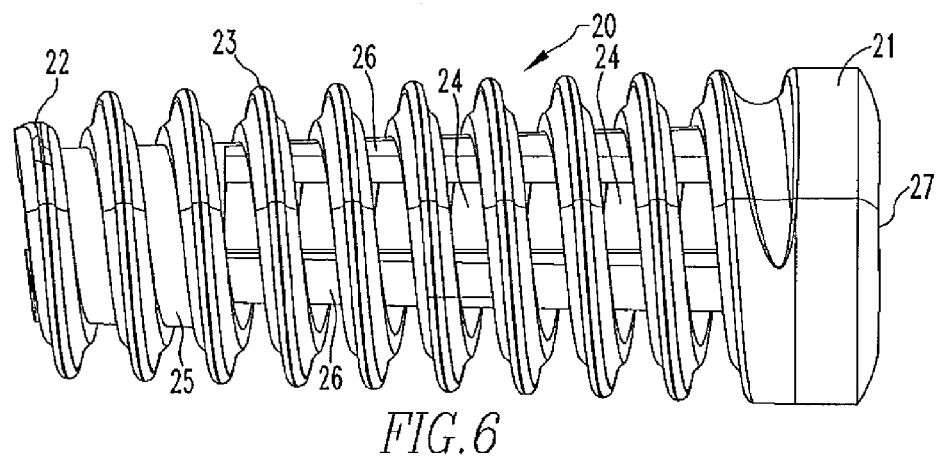
FIG. 6 shows a side view of the screw of FIG. 5.
Figure 7:
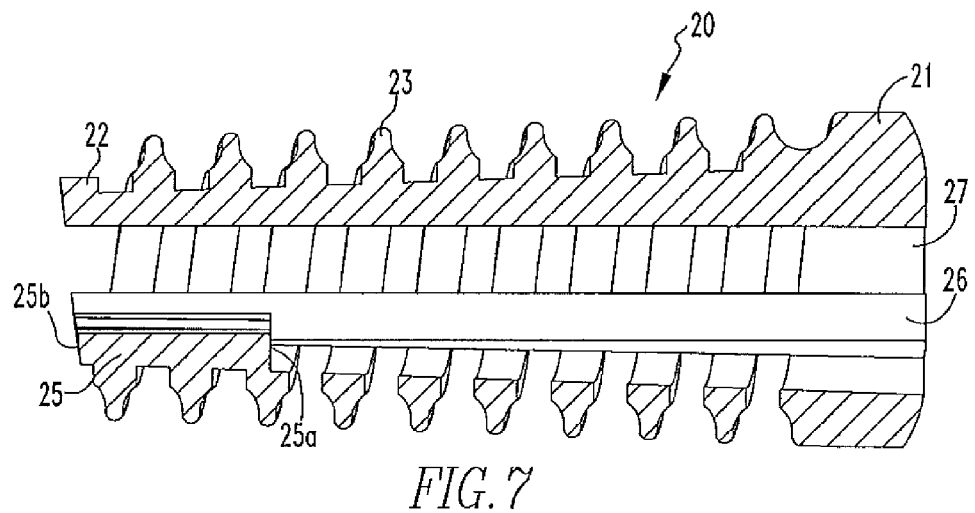
FIG. 7 shows a cross-sectional view of the screw of FIG. 6.
Figure 8:
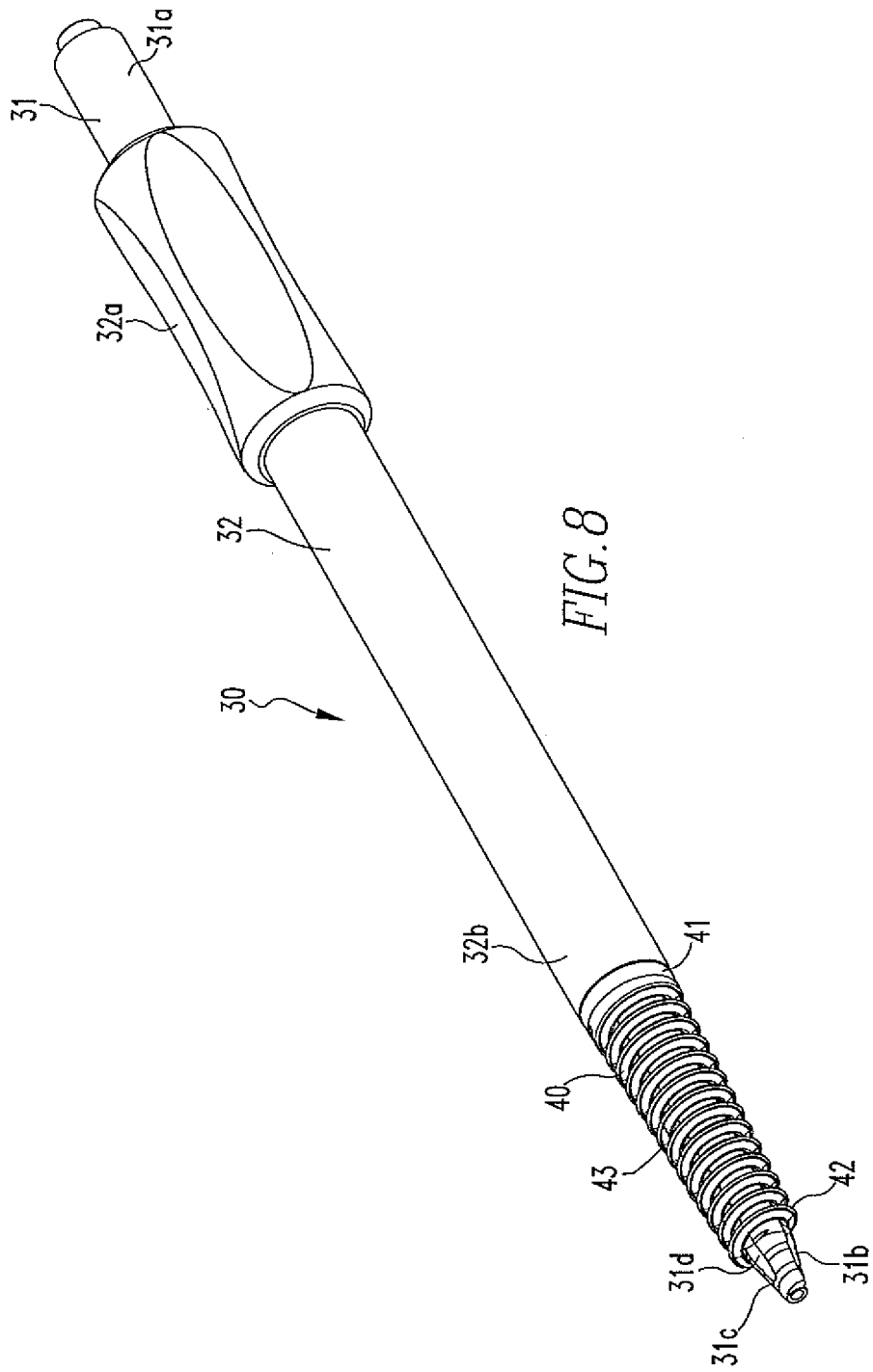
FIG. 8 shows a second embodiment of a shaft of the present disclosure.
Figure 9A:
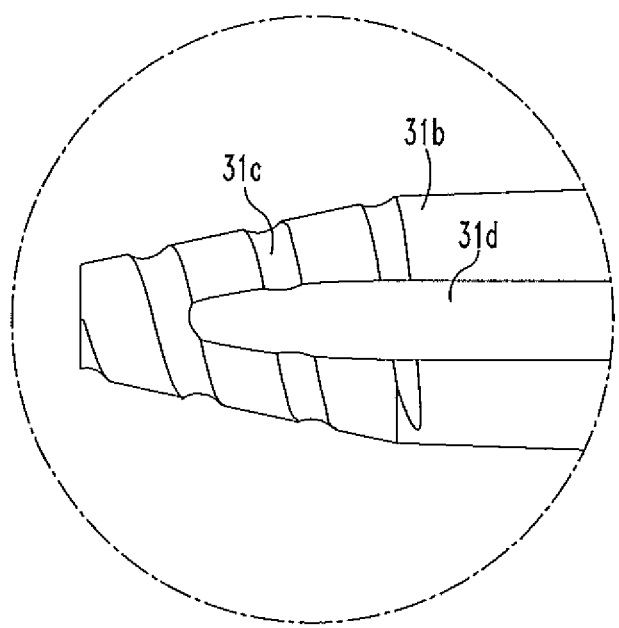
FIG. 9A shows an exploded view of the distal end of the inner member of FIG. 9.
Figure 11:
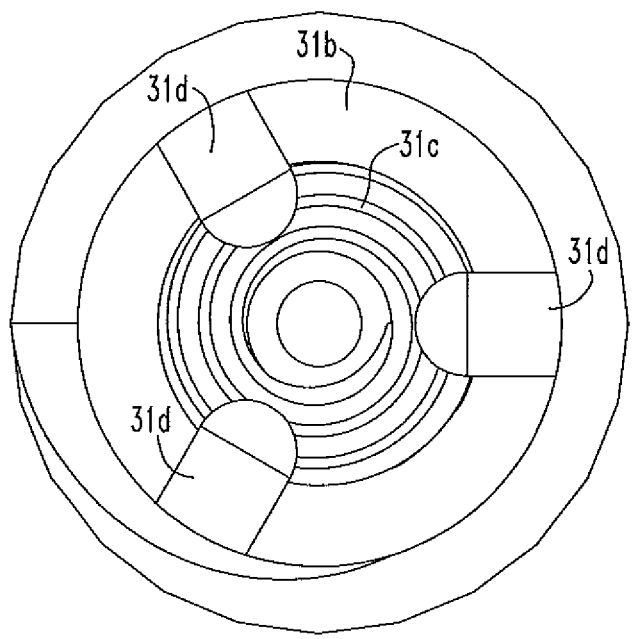
FIG. 11 shows a front view of the distal end of the inner member of FIG. 9.
Figure 16:
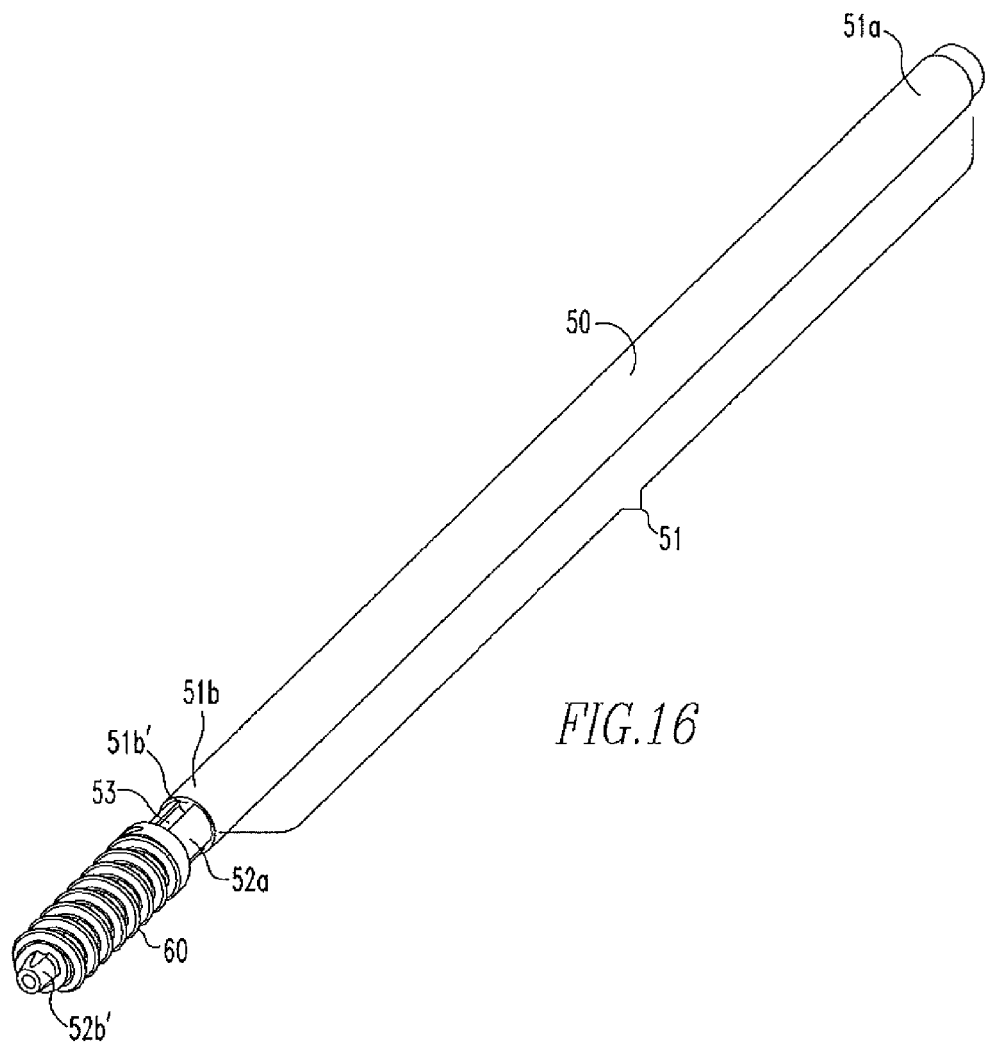
FIG. 16 shows an isometric view of a third embodiment of a shaft of the present disclosure and a screw for use with the shaft.
Figure 17:
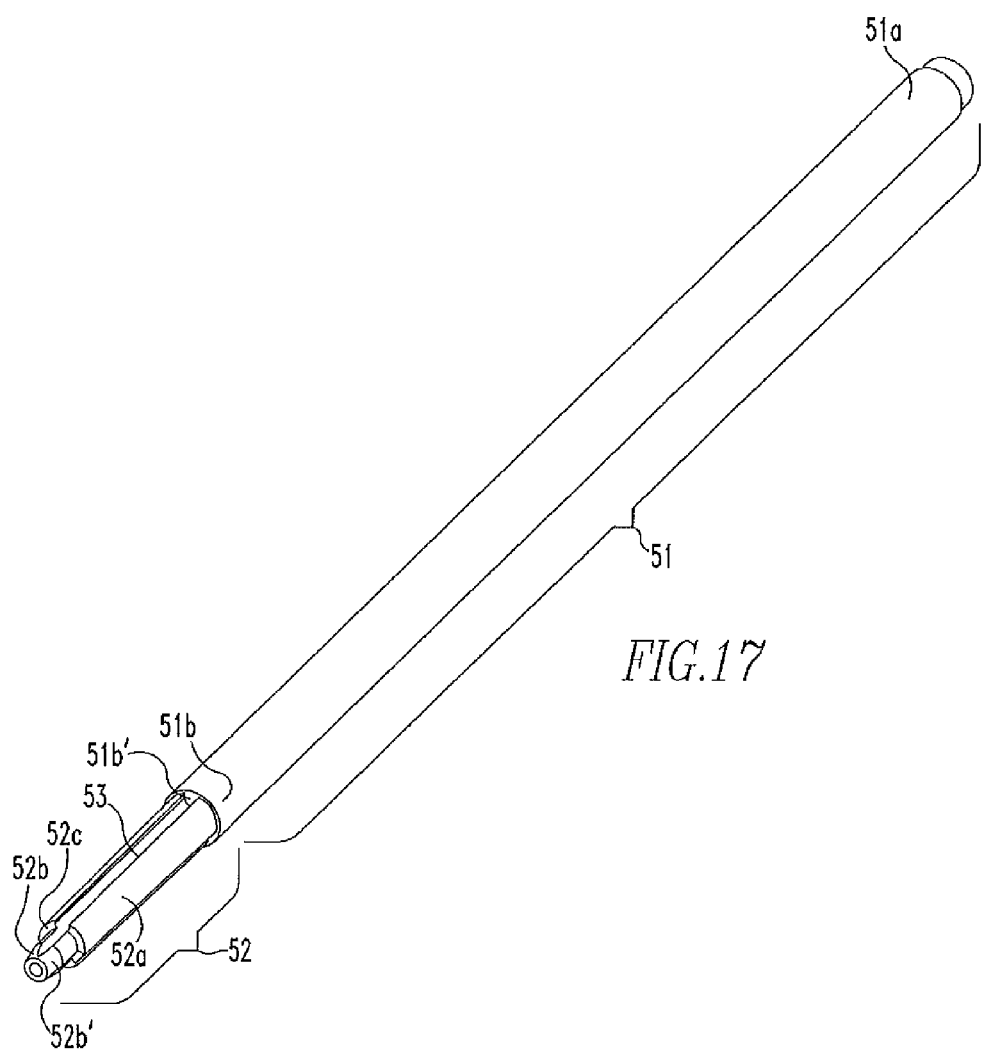
FIG. 17 shows an isometric view of the shaft of FIG. 16.
Figure 18:
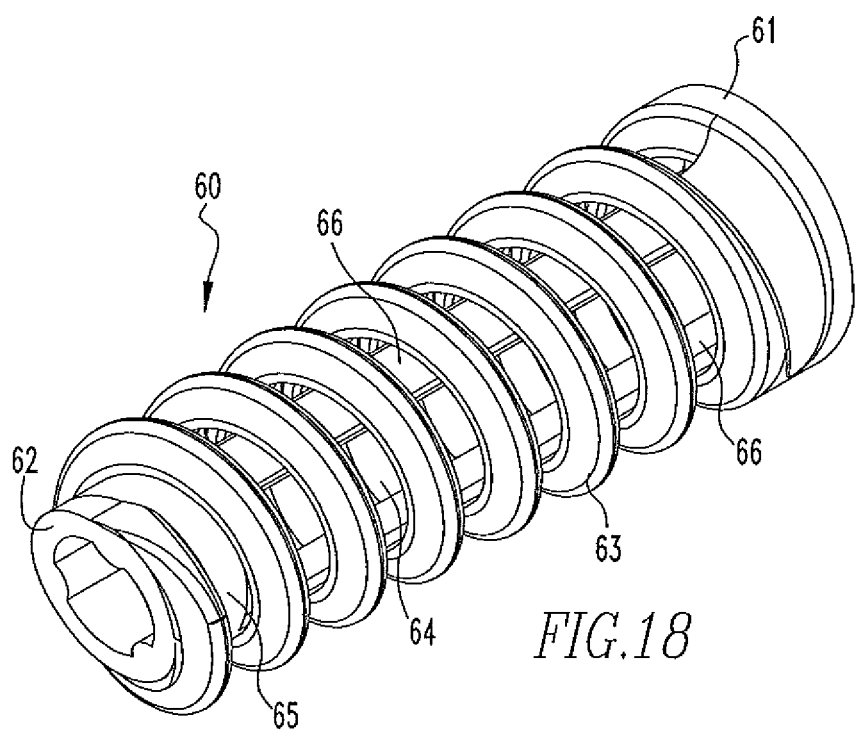
FIG. 18 shows an isometric view of the screw of FIG. 16.
Figure 19:
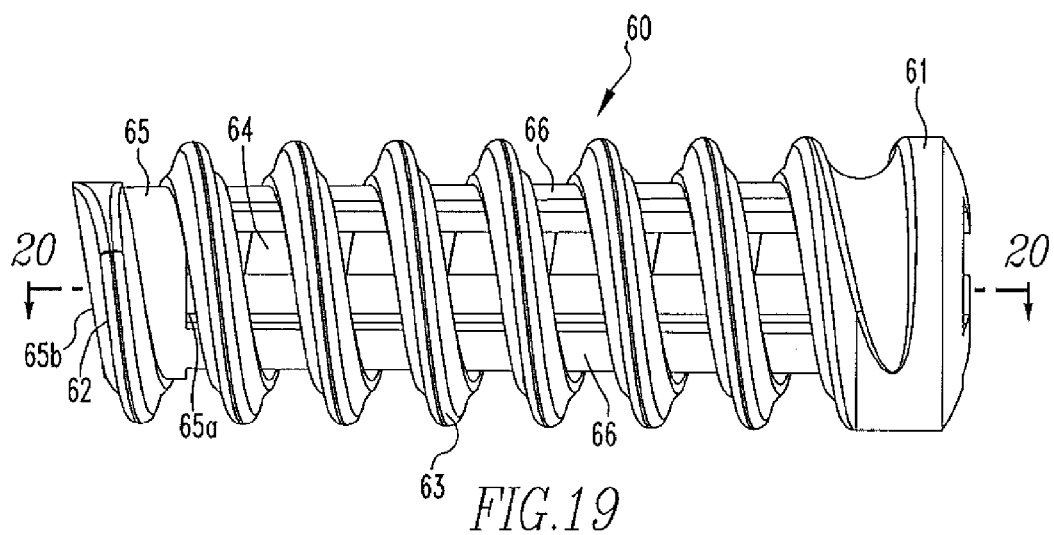
FIG. 19 shows a side view of the screw of FIG. 16.
Figure 20:
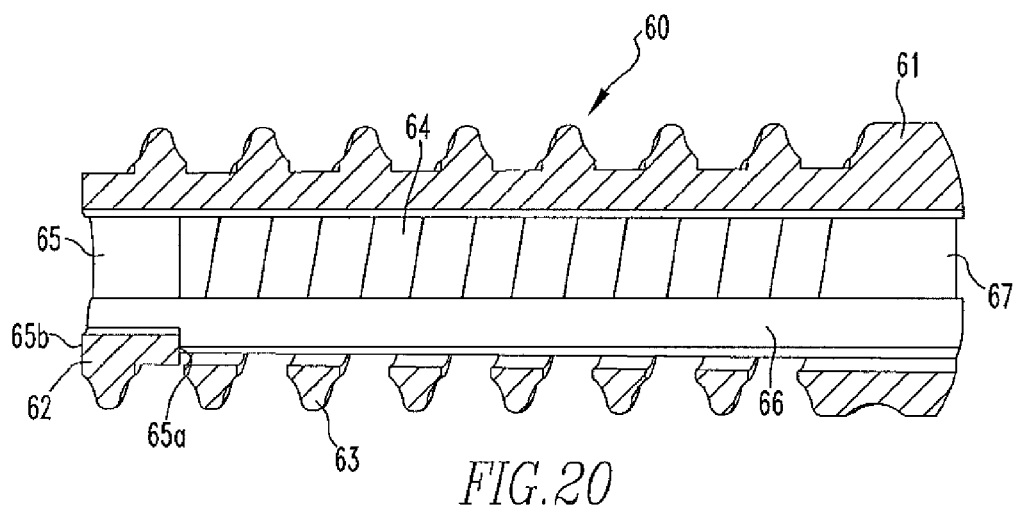
FIG. 20 shows a cross-sectional view of the screw of FIG. 19.

FIGS. 5-7 show the screw 20 for use with the delivery device 10 of the present disclosure. The screw 20 includes a proximal end 21 and a distal end 22. A majority of the screw 20 includes screw threads 23 in the form of an open helical coil, i.e. a connected series of continuous regularly spaced turns extending in a helical or spiral form substantially from the proximal end 21 to the distal end 22 with apertures 24 being defined by the space between the turns of the coil. In other words, interference screw 20 may include an open helical coil defining an internal volume, with the internal volume communicating with the region exterior to the open helical coil through the spacing between the turns of the open helical coil. The distal end 22 also includes a depth stop 25 that extends a partial length of the screw 20. The depth stop 25 includes a proximal end 25a and a distal end 25b. Additionally, a plurality of longitudinally-extending runners 26 extend along the interior of the screw threads 23.

The distal end 12b of the shaft 12 is placed within the interior of the screw 20, via the opening 27, until the proximal end 25a of the depth stop 25 engages the depth stop 12e of the shaft 12. During insertion of the shaft 12 into the screw 20, the runners 26 engage the grooves 12d and become housed within the grooves 12d. As shown in FIG. 1, the distal end 12b of the shaft 12 also includes hash marks 12f, each of which is associated with a number 12g. Once the screw 20 is placed on the shaft 12, the proximal end 21 of the screw 20 aligns with one of the hash marks/numbers 12f, thereby indicating the length of the screw 20.

FIGS. 8, 9-9A, and 10-15 show an alternative shaft 30 of the present disclosure. The shaft 30 includes an inner member 31 and an outer member 32 disposed over the inner member 31. The proximal end 31a of the inner member 31 is similar in shape to the proximal end 12a of the shaft 12. The distal end 31b of the inner member 31 includes threads 31c. Grooves 31d extend along the member 31 and intersect the threads 31c. Additionally, threads 31e are located between the proximal and distal ends 31a,31b of the member 31. The outer member 32 includes a first section 32a and a second section 32b. The first section 32a has a larger diameter than the second section 32b. The first section 32a also includes threads 32c on an inner wall 32d of the outer member 32.

Once the outer member 32 is disposed over the inner member 31, threads 32c engage threads 31e to move the outer member 32 relative to the inner member 31. Moving the outer member 32 relative to the inner member 31 allows for more or less of the distal end 31b of the inner member 31 to be shown. Similar to the distal end 12b of the shaft 12, the distal end 31b of inner member 31 includes hash marks/numbers (not shown) that align with an end 32b' of the second section 32b, thereby indicating a length of screw 40 that will be disposed on the distal end 31b of the inner member 31. As shown in FIGS. 14 and 15, the outer member 32 is located at different positions along the length of the inner member 31 to allow for screws 40 of different lengths to be loaded on the distal end 31b of the inner member 31.

A handle assembly, similar to the handle assembly 11, is coupled to the proximal end 31a of the inner member 31. Similar to screw 20, screw 40 includes a proximal end 41 and a distal end 42. The screw 40 includes screw threads 43 in the form of an open helical coil having an interior and a plurality of longitudinally-extending runners 45 extending along the interior of the screw threads 43. Screw 40 is more fully described in United States Patent Application Publication No. 20080154314, the disclosure of which is incorporated herein by reference in its entirety. Once the outer member 32 has been moved to indicate the screw length, the screw 40 is loaded onto the distal end 31b, such that a proximal end 41 of the screw 40 engages the end 32b' and the runners 45 engage the grooves 31d and become housed within the grooves 31d.

FIGS. 16-20 show another alternative embodiment of the shaft 50 and screw 60 of the present disclosure. The shaft 50 includes a first portion 51 including a proximal end 51a and a distal end 51b and a second portion 52 including a first area 52a and a second area 52b. The proximal end 51a is configured to be coupled to a handle assembly, similar to the handle assembly 11. However, other handle assemblies may be used. The first area 52a has a smaller diameter than the first portion 51, such that a first depth stop 51b' exists at the distal end 51b of the first portion 51. The second area 52b has a smaller diameter than the first area 52a such that a second depth stop 52c exists between the first area 52a and the second area 52b. An end 52b' of the second area 52b is tapered to allow for easier insertion of the anchor 60 into a bone during ligament reconstruction surgery, as will be further described below. The second portion 52 also includes grooves 53 extending between the first and second areas 52a,52b. For the purposes of this disclosure, there are three grooves 53. However, the second portion 52 may include a higher or lower number of grooves 53.

Similar to screw 20 shown in FIGS. 5-7, screw 60 includes a proximal end 61 and a distal end 62. A majority of the screw 60 includes screw threads 63 in the form of an open helical coil, i.e. a connected series of continuous regularly spaced turns extending in a helical or spiral form substantially from the proximal end 61 to the distal end 62 with apertures 64 being defined by the space between the turns of the coil. In other words, interference screw 60 may include an open helical coil defining an internal volume, with the internal volume communicating with the region exterior to the open helical coil through the spacing between the turns of the open helical coil. The distal end 62 also includes a depth stop 65 that extends a partial length of the screw 60. The depth stop 65 includes a proximal end 65a and a distal end 65b. Unlike the open depth stop 25 of screw 20 most clearly shown in FIG. 5, the depth stop 65 of screw 60 is a closed depth stop, most clearly shown in FIG. 18. Additionally, a plurality of longitudinally-extending runners 66 extend along the interior of the screw threads 63.

The second portion 52 of the shaft 50 is placed within the interior of the screw 60, via the opening 67, until the proximal end 65a of the depth stop 65 engages the second depth stop 52c of the shaft 50. During insertion of the shaft 50 into the screw 60, the runners 66 engage the grooves 53 and become housed within the grooves 53. The screws 60 may be of a variety of lengths. For example, a screw 60 may be of such length that its proximal end 61 would engage the first depth stop 51b'.

As described above, during ligament reconstruction surgery, the end of the graft ligament is placed in the bone tunnel and then the interference screw 20,40,60 is advanced into the bone tunnel via the use of shafts 12,30,50 so that the interference screw 20,40,60 extends parallel to the bone tunnel and simultaneously engages both the graft ligament and the side wall of the bone tunnel. The screws 20,40,60 may be used in either the femoral or tibial tunnels. Methods of ligament reconstruction via use of the screws 20,40,60 is further shown in the '314 publication shown above.

Figure 21:
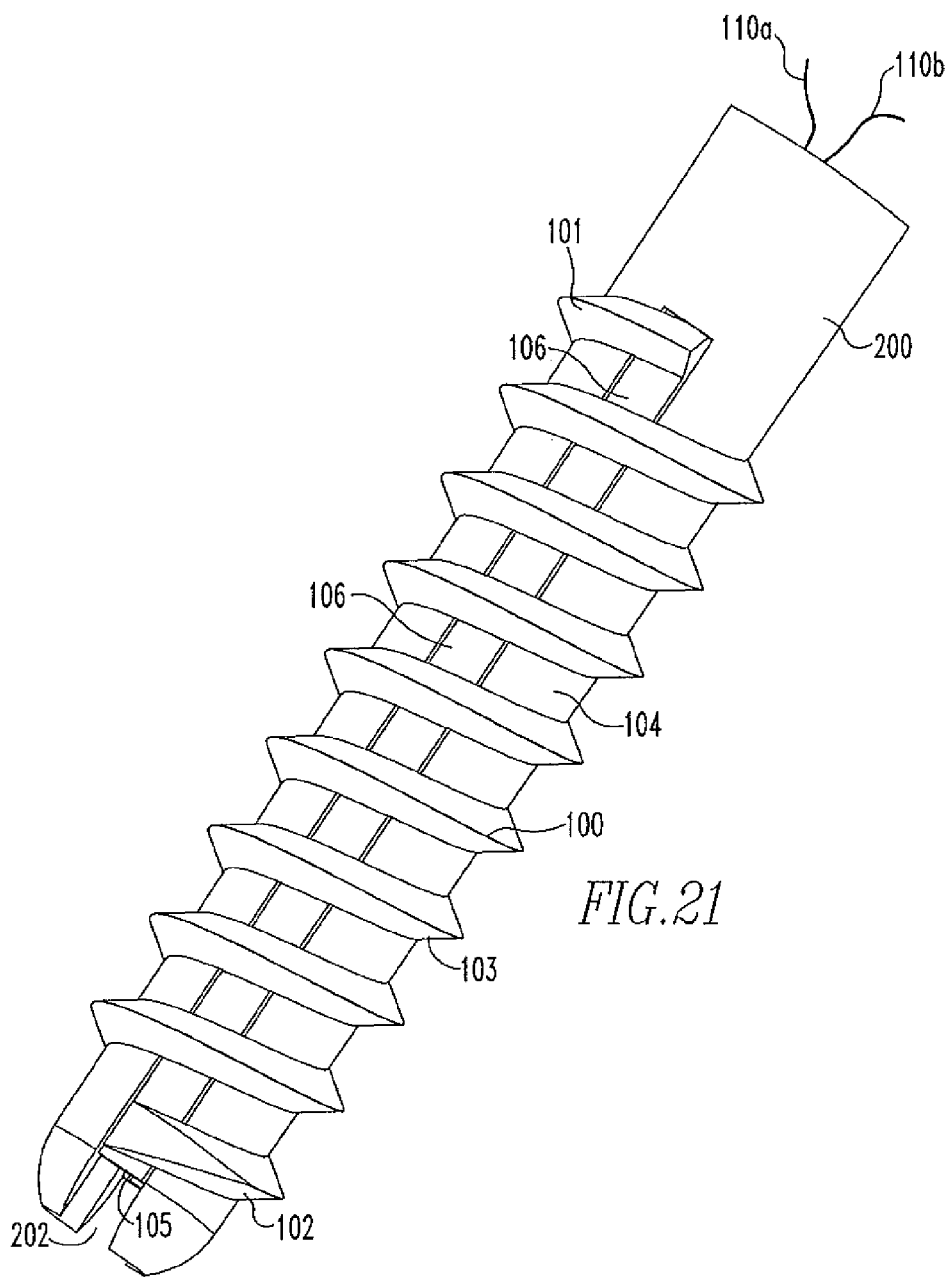
FIG. 21 shows an isometric view of a fourth embodiment of a shaft of the present disclosure and a screw for use with the shaft.
Figure 22:
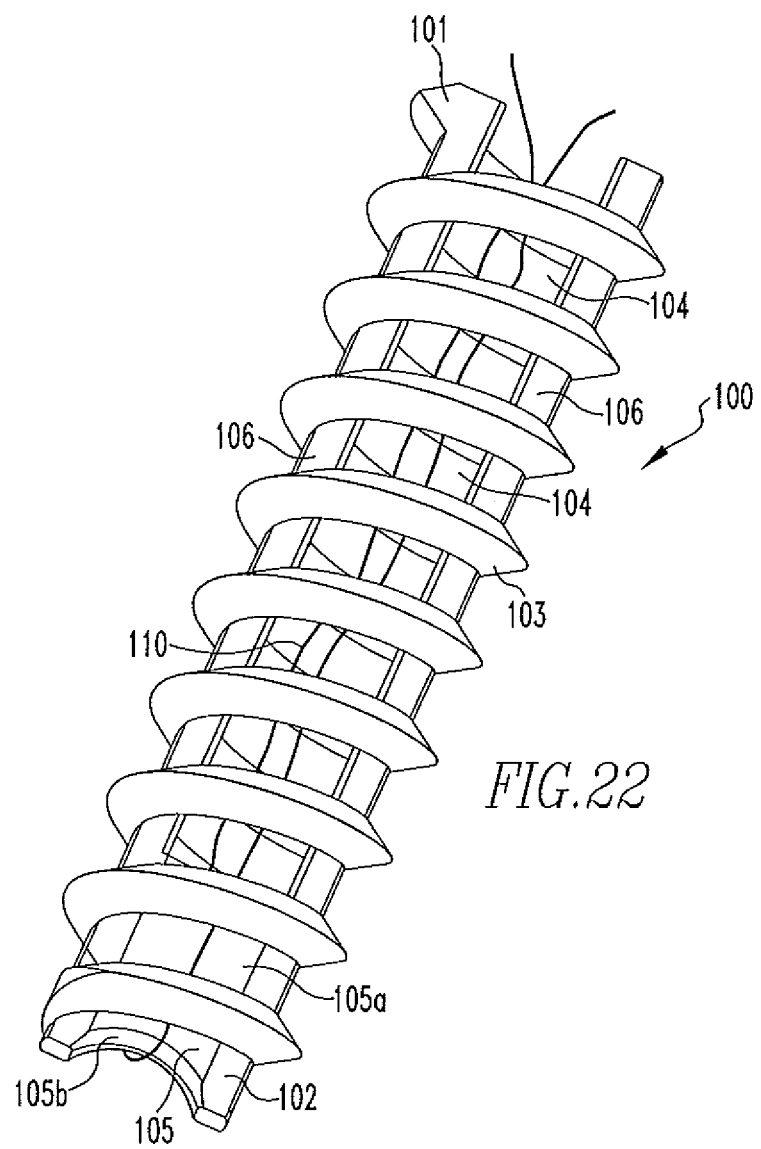
FIG. 22 shows an isometric view of the screw of FIG. 21.

FIGS. 21-23 show yet another alternative embodiment of the screw 100 and the delivery device 200 of the present disclosure. The screw 100 includes a proximal end 101 and a distal end 102. A majority of the screw 100 includes screw threads 103 in the form of an open helical coil, i.e. a connected series of continuous regularly spaced turns extending in a helical or spiral form substantially from the proximal end 101 to the distal end 102 with apertures 104 being defined by the space between the turns of the coil. In other words, interference screw 100 may include an open helical coil defining an internal volume, with the internal volume communicating with the region exterior to the open helical coil through the spacing between the turns of the open helical coil. The distal end 102 also includes a suture bridge 105 that extends a partial length of the screw 100. The suture bridge 105 includes a proximal end 105a and a distal end 105b. The distal end 105b includes a concave shape. A flexible member 110, such as a suture, is housed within the screw 100, such that the suture 110 extends around the distal end 105b of the bridge 105. Additionally, longitudinally-extending runners 106 extend from the suture bridge 105 and along the interior of the screw threads 103. For the purposes of this disclosure, there are two longitudinally extending runners 106. However, more or less than two runners are within the scope of this disclosure.

The delivery device 200 includes a distal end 201 having a slot 202 and grooves 203 extending from the slot 202 on each side of the device 200. As shown in FIG. 21, the screw 100 is located on the distal end 201 such that the suture bridge 105 is housed within the slot 202 and the runners 106 are housed within the grooves 203. The delivery device 200 is cannulated, such that when the screw 100 is located on the device 200, the suture ends 110a,110b extend through the cannulation 204.

FIGS. 24-26 show a screw 300 similar to screw 100. However, screw 300 additionally includes a pointed tip 311 located on the distal end 302. The tip 311 includes a through hole 312. The hole 312 helps in locating the suture 110 within the interior of the screw 300. As shown in FIG. 24, the screw 300 is located on the distal end 201 of delivery device 200 such that the suture bridge 305 is housed within the slot 202 and the runners 306 are housed within the grooves 203. As stated above, the delivery device 200 is cannulated, such that when the screw 300 is located on the device 200, the suture ends 110a,110b extend through the cannulation 204, as shown in FIG. 24.

For clarity purposes, only the distal end 201 of the device 200 is shown. However, the device 200 would include a proximal end, similar to the devices above, which may be coupled to a handle assembly, similar to handle assembly 11 above. The screws 100,300 are used in the repair of soft tissue, specifically when the to re-attach tissue to bone. One example of this repair is when the screw 100,300 is delivered into bone via the use of device 200, the device 200 is removed from screw 100,300, the tissue is placed on the bone to be adjacent the screw 100,300, the suture ends 110a,110b are pulled through the tissue, and then the suture ends 110a,110b are tied. A hole may be made in the bone prior to insertion of the screw 100,300 into the bone. However, screw 300 may be inserted into bone without first making a hole in the bone. In this case, the pointed tip 311 is used to start insertion of the screw 300 into the bone and then rotary motion may be used to complete insertion of the screw 300 into the bone. Other methods of tissue repair via use of these screws and delivery device may also be used.

The handle 11a of handle assembly 11 is made from plastic, however, other non-metal and metal materials may also be used. The shape and size of handle 11a may be any shape and size necessary to help facilitate insertion of the screw 20 into bone. The coupler 11b is made from a metal material, such as stainless steel or titanium, but may be made from other metal and non-metal materials that are strong enough to withstand the forces applied during surgery. The coupler 11b is press-fit to the handle 11a, but may be coupled to the handle 11a in any other manner known to those of skill in the art. The size and shape of the coupler 11b may be any size and shape necessary to help facilitate insertion of the screw 20 into bone. The channel 11b' may be any length necessary and the opening 11b" may be any shape necessary to facilitate coupling of the shaft 12 to the coupler 11b.

The shaft 12 is made from a metal material, such as stainless steel and titanium, however, other metal and non-metal materials that would withstand the forces applied during surgery may be used. The diameter of the shaft 12 may vary. The proximal end 12a of the shaft 12 may be any shape necessary to facilitate insertion of the end 12a through opening 11b" and into channel 11b'. The number of threads 12c and grooves 12d may vary and the lengths of the grooves 12d may also vary. The location of depth stop 12e may also vary based on the diameter of the shaft 12 and the diameter of the screw 20 that is used. The grooves 12d, depth stop 12e, and threads 12c may be formed by any method known to one of skill in the art.

The screw 20 is made from a polymer material via a molding method. However, other material, which would allow the screw 20 to withstand forces applied during surgery, and other methods of making may be used. The depth stop 25 is open ended and doesn't extend the entire inner diameter of the screw 20. The amount of screw inner diameter that the depth stop 25 covers may vary and the length of the depth stop 25 may vary based on the diameter of the screw. The number and length of the runners 26 may also vary. Once the screw 20 is located on the shaft 12, the distal end 12b of the shaft 12 extends from the distal end 22 of the screw 20. During insertion of the screw 20 into bone, the threads 12c create threads in the bone, thereby creating a seat for the screw threads 23, as described more fully in the '314 publication. The amount of the distal end 12b of the shaft 12 that extends from the distal end 22 of the screw 20 may vary.

The diameters of the first and second sections 32a,32b of outer member 32 may vary and the number of threads 32c may also vary. The number of threads 31c,31e and grooves 31d may vary and the lengths of the grooves 31d may also vary. The inner and outer members 31,32 are made from a metal material, such as stainless steel and titanium, and via a method known to one of skill in the art. However, other materials may also be used. The screw 40 is made from a polymer material via a molding method. However, other material and methods of making may be used. The number and length of the runners 45 may also vary. Once the screw 40 is located on the shaft 30, the distal end 31b of the shaft 30 extends from the distal end 42 of the screw 40. During insertion of the screw 40 into bone, the threads 31c create threads in the bone, thereby creating a seat for the screw threads 43, as described more fully in the '314 publication. The amount of the distal end 31b of the shaft 30 extending from the screw 40 may vary.

The shaft 50 is made from a metal material, such as stainless steel or titanium, but may be made from another metal material or a non-metal material that is strong enough to withstand the force applied to the shaft 50 during surgery. The shaft 50 may be made via a method known to one of skill in the art. The diameters of the first and second portions 51,52 may vary along with the number and lengths of the grooves 53 and the locations of the depth stops 52c,51b' may vary based on the diameter of the screw 60 or other factors. Rather than being tapered, the end 52b' may be designed in another manner to allow easier insertion of the screw 60 into bone. The screw 60 is made from a polymer material via a molding method. However, other material, which would allow the screw to withstand the forces applied during surgery, and other methods of making may be used. The number and length of the runners 66 may also vary. Once the screw 60 is located on the shaft 50, the second portion 52 of the shaft 50 extends from the distal end 62 of the screw 60. The amount of the second portion 52 extending from the screw 60 may vary. Additionally, the length of the depth stop 65 may also vary based on the diameter of the screw 60 or other factors.

The delivery device 200 is made from a metal material, such as stainless steel or titanium, but may be made from a non-metal material that is strong enough to withstand the forces applied to the device 200 during surgery. The delivery device 200 is made via a method known to one of skill in the art. The screws 100,300 are made from a polymer material and via a molding process, however, other material, which would allow the screw to withstand the forces applied during surgery, and other processes known to one of skill in the art may be used. The suture bridge 105 may have a distal end 105b having a shape other than concave and the length of the suture bridge 105, the slot 202, and the grooves 203 may vary. The size and the shape of the hole 312 may vary.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. An interference screw comprising: a proximal end and a distal end, the screw including threads extending in an open helical form from the proximal end to the distal end, a depth stop extending a partial length of the screw from a distal terminal end, and a plurality of runners extending longitudinally along an interior of the screw, wherein the depth stop of the screw is configured to engage a depth stop of a delivery device such that a distal end of the delivery device extends beyond the distal end of the screw.

2. The interference screw of claim 1 wherein the screw is made from a polymer material.

3. The interference screw of claim 1 wherein the depth stop is an open depth stop encircling part of the distal end of the screw.

4. The interference screw of claim 1 wherein the depth stop is an closed depth stop encircling the distal end of the screw.

5. The interference screw of claim 1 wherein the proximal end of the screw aligns with a hash mark on the distal end of the delivery device and a number associated with the hash mark identifies the length of the screw.

6. The interference screw of claim 1 wherein each of the plurality of runners has a cross sectional shape based on a semi-circle.

7. The interference screw of claim 1 wherein the plurality of runners includes three runners.

8. A delivery device and screw combination comprising:
a delivery device comprising a handle assembly, the assembly including a handle and a connector coupled to the handle, the connector including a channel and an opening to the channel; and a shaft coupled to the handle, the shaft including a proximal end and a distal end, the distal end including threads, grooves intersecting the threads, and a depth stop; and
an interference screw coupled to the delivery device comprising a proximal end and a distal end, the screw including threads extending in an open helical form from the proximal end to the distal end, a depth stop extending a partial length of the screw from a distal terminal end, and a plurality of runners extending longitudinally along an interior of the screw, the screw located on the distal end of the delivery device such that a proximal end of the depth stop of the screw engages the depth stop of the delivery device and the distal end of the delivery device extends beyond the distal end of the screw.

9. The delivery device and screw combination of claim 8 wherein the screw is made from a polymer material.

10. The delivery device and screw combination of claim 8 wherein the depth stop of the screw is an open depth stop encircling part of the distal end of the screw.

11. The delivery device and screw combination of claim 8 wherein the depth stop of the screw is an closed depth stop encircling the distal end of the screw.

12. The delivery device and screw combination of claim 8 wherein the distal end of delivery device further includes hash marks and the proximal end of the screw aligns with one of the hash marks and a number associated with the one hash mark identifies the length of the screw.

13. The delivery device and screw combination of claim 8 wherein each of the plurality of runners has a cross-sectional shape based on a semi-circle; and
wherein each of the grooves of the delivery device has a shape that is the inverse of the cross-sectional shape of a runner.

14. The delivery device and screw combination of claim 8 wherein the plurality of runners includes three runners.

15. The delivery device and screw combination of claim 8 wherein the delivery device is made from stainless steel or titanium.

16. The delivery device and screw combination of claim 8 wherein the opening of the connector of the delivery device is in the shape of a "D."

17. A method for assembling a combination of a delivery device and a screw, the method comprising:
inserting a distal end of a delivery device into an opening defined by a proximal end of a screw, the distal end of the delivery device including threads, grooves intersecting the threads, and a depth stop, the screw including threads extending in an open helical form from the proximal end of the screw to a distal end of the screw;
engaging a plurality of runners extending longitudinally along an interior of the screw with the grooves of the delivery device; and
engaging a depth stop of the screw, which extends a partial length of the screw from a distal terminal end, with the depth stop of the delivery device such that the distal end of the delivery device extends beyond the distal end of the screw.

* * * * *